United States Patent
Pastore et al.

(10) Patent No.: US 8,521,288 B2
(45) Date of Patent: Aug. 27, 2013

(54) APPARATUS AND METHOD FOR TEMPORARY TREATMENT OF ACUTE HEART FAILURE DECOMPENSATION

(75) Inventors: Joseph M. Pastore, Concord, OH (US); Qingsheng Zhu, Wexford, PA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 951 days.

(21) Appl. No.: 12/151,569

(22) Filed: May 7, 2008

(65) Prior Publication Data

US 2008/0215104 A1 Sep. 4, 2008

Related U.S. Application Data

(63) Continuation of application No. 11/044,971, filed on Jan. 27, 2005, now Pat. No. 7,386,345.

(51) Int. Cl.
*A61N 1/00* (2006.01)

(52) U.S. Cl.
USPC ............ 607/30; 607/32; 607/37; 607/59; 607/60; 607/62; 607/115; 607/116; 607/119

(58) Field of Classification Search
USPC ............ 607/30, 32, 37, 59–60, 62, 115–116, 607/119
See application file for complete search history.

(56) References Cited

U.S. PATENT DOCUMENTS

| | | | |
|---|---|---|---|
| 5,129,394 A | 7/1992 | Mehra | |
| 5,330,505 A | 7/1994 | Cohen | |
| 5,368,040 A | 11/1994 | Carney | |
| 5,720,770 A * | 2/1998 | Nappholz et al. | ............... 607/30 |
| 5,743,267 A | 4/1998 | Nikolic et al. | |
| 5,758,652 A | 6/1998 | Nikolic | |
| 5,788,643 A | 8/1998 | Feldman | |
| 5,792,197 A | 8/1998 | Nappholz | |

(Continued)

FOREIGN PATENT DOCUMENTS

| | | |
|---|---|---|
| EP | 1118307 A1 | 7/2001 |
| EP | 1348463 A1 | 10/2003 |

(Continued)

OTHER PUBLICATIONS

"U.S. Appl. No. 11/044,971, Response filed Jun. 12, 2007 to Non-Final Office Action mailed Apr. 9, 2007", 11 pgs.

(Continued)

*Primary Examiner* — Deborah Malamud

(74) *Attorney, Agent, or Firm* — Schwegman Lundberg & Woessner, P.A.

(57) ABSTRACT

A system for providing temporary therapy, such as cardiac resynchronization therapy, to a patient suffering a decompensation event. The system can include a device having an external module for generating electrical stimuli, a first lead coupled to the module and implanted into an atrial region of a patient's heart, and a second lead coupled to the module and implanted into a ventricular region of the patient's heart. The device can also include a storage module coupled to the external module to store data associated with physiological data measured by the device. The external module is configured to temporarily generate electrical stimuli that are delivered by at least one of the first and second leads to provide therapy cardiac resynchronization therapy to the heart. A network can be coupled to the device to allow data stored in the device to be downloaded through the network to a central repository.

25 Claims, 4 Drawing Sheets

(56) References Cited

U.S. PATENT DOCUMENTS

| | | |
|---|---|---|
| 5,876,353 A | 3/1999 | Riff |
| 5,957,861 A | 9/1999 | Combs et al. |
| 5,974,340 A | 10/1999 | Kadhiresan |
| 6,021,351 A | 2/2000 | Kadhiresan et al. |
| 6,102,874 A | 8/2000 | Stone et al. |
| 6,104,949 A | 8/2000 | Pitts Crick et al. |
| 6,129,744 A | 10/2000 | Boute |
| 6,135,970 A | 10/2000 | Kadhiresan et al. |
| 6,223,082 B1 | 4/2001 | Bakels et al. |
| 6,246,910 B1 | 6/2001 | Bonnet et al. |
| 6,275,727 B1 | 8/2001 | Hopper et al. |
| 6,277,078 B1 | 8/2001 | Porat et al. |
| 6,314,323 B1 | 11/2001 | Ekwall |
| 6,328,699 B1 | 12/2001 | Eigler et al. |
| 6,360,123 B1 | 3/2002 | Kimchi et al. |
| 6,371,922 B1 | 4/2002 | Baumann et al. |
| 6,409,675 B1 | 6/2002 | Turcott |
| 6,438,408 B1 | 8/2002 | Mulligan et al. |
| 6,454,707 B1 | 9/2002 | Casscells, III et al. |
| 6,454,719 B1 | 9/2002 | Greenhut |
| 6,456,880 B1 | 9/2002 | Park et al. |
| 6,459,929 B1 | 10/2002 | Hopper et al. |
| 6,459,934 B1 | 10/2002 | Kadhiresan |
| 6,473,640 B1 | 10/2002 | Erlebacher |
| 6,473,646 B2 | 10/2002 | Sun et al. |
| 6,473,647 B1 | 10/2002 | Bradley |
| 6,480,733 B1 | 11/2002 | Turcott |
| 6,480,742 B2 | 11/2002 | Stahmann et al. |
| 6,488,677 B1 | 12/2002 | Bowman et al. |
| 6,491,639 B1 | 12/2002 | Turcott |
| 6,512,949 B1 | 1/2003 | Combs et al. |
| 6,529,772 B2 | 3/2003 | Carlson et al. |
| 6,539,249 B1 | 3/2003 | Kadhiresan et al. |
| 6,561,984 B1 | 5/2003 | Turcott |
| 6,572,557 B2 | 6/2003 | Tchou et al. |
| 6,575,912 B1 | 6/2003 | Turcott |
| 6,580,946 B2 | 6/2003 | Struble |
| 6,589,188 B1 | 7/2003 | Street et al. |
| 6,595,927 B2 | 7/2003 | Pitts-Crick et al. |
| 6,600,949 B1 | 7/2003 | Turcott |
| 6,622,040 B2 | 9/2003 | Ding et al. |
| 6,641,542 B2 | 11/2003 | Cho et al. |
| 6,643,548 B1 | 11/2003 | Mai et al. |
| 6,645,153 B2 | 11/2003 | Kroll et al. |
| 6,668,188 B2 | 12/2003 | Sun et al. |
| 6,668,194 B2 | 12/2003 | VanHout |
| 6,701,186 B2 | 3/2004 | Spinelli et al. |
| 6,738,667 B2 | 5/2004 | Deno et al. |
| 6,760,622 B2 | 7/2004 | Helland et al. |
| 6,763,267 B2 | 7/2004 | Ding |
| 6,795,732 B2 | 9/2004 | Stadler et al. |
| 6,804,555 B2 | 10/2004 | Warkentin |
| 6,829,503 B2 | 12/2004 | Alt |
| 6,859,662 B2 | 2/2005 | Bombardini |
| 6,885,889 B2 | 4/2005 | Chinchoy |
| 6,928,324 B2 | 8/2005 | Park et al. |
| 6,952,611 B2 | 10/2005 | Sun et al. |
| 6,959,214 B2 | 10/2005 | Pape et al. |
| 6,961,615 B2 | 11/2005 | Kroll et al. |
| 6,980,851 B2 | 12/2005 | Zhu et al. |
| 7,113,825 B2 | 9/2006 | Pastore et al. |
| 7,115,095 B2 | 10/2006 | Eigler et al. |
| 7,127,290 B2 | 10/2006 | Girouard et al. |
| 7,137,953 B2 | 11/2006 | Eigler et al. |
| 7,146,208 B2 | 12/2006 | Holmstrom et al. |
| 7,386,345 B2 | 6/2008 | Pastore et al. |
| 2002/0002389 A1 | 1/2002 | Bradley et al. |
| 2003/0028221 A1 | 2/2003 | Zhu et al. |
| 2003/0157493 A1 | 8/2003 | Sklar et al. |
| 2003/0199933 A1 | 10/2003 | Struble et al. |
| 2003/0199956 A1 | 10/2003 | Struble et al. |
| 2006/0167511 A1 | 7/2006 | Pastore et al. |

FOREIGN PATENT DOCUMENTS

| | | |
|---|---|---|
| WO | WO-9739792 A1 | 10/1997 |
| WO | WO-0240096 A1 | 5/2002 |
| WO | WO-03089033 A1 | 10/2003 |

OTHER PUBLICATIONS

"U.S. Appl. No. 11/044,971, Response filed Jan. 14, 2008 to Final Office Action mailed Aug. 14, 2007", 4 pgs.

"U.S. Appl. No. 11/044,971, Response filed Dec. 20, 2006 to Non-Final Office Action mailed Sep. 25, 2006", 10 pgs.

"U.S. Appl. No. 11/044,971 Notice of Allowance mailed Feb. 1, 2008", 6 pgs.

"U.S. Appl. No. 11/044,971 Non-Final Office Action mailed Apr. 9, 2007", 6 pgs.

"U.S. Appl. No. 11/044,971 Non-Final Office Action mailed Sep. 25, 2006", 7 pgs.

"Final office Action mailed Aug. 14, 2007 in U.S. Appl. No. 11/044,971", 6 pgs.

Nelson, Gregory S., "Left ventricular or biventricular pacing improves cardiac function at diminished energy cost in patients with dilated cardiomyopathy and left bundle-branch block", *Circulation*, 102(25), (Dec. 19, 2000),3053-3059.

* cited by examiner

APPARATUS AND METHOD FOR TEMPORARY TREATMENT OF ACUTE HEART FAILURE DECOMPENSATION

CROSS REFERENCE TO RELATED APPLICATION

This application is a continuation of U.S. application Ser. No. 11/044,971, issued as U.S. Pat. No. 7,386,345, filed Jan. 27, 2005, the specification of which is herein incorporated by reference.

TECHNICAL FIELD

The present invention is directed to systems and methods for providing therapy for congestive heart failure. More specifically, the present invention is directed to systems and methods for providing temporary therapy for acute heart failure decompensation.

BACKGROUND

The heart is a muscular organ comprising multiple chambers that operate in concert to circulate blood throughout the body's circulatory system. As shown in FIG. 1, the heart 100 includes a right-side portion or pump 102 and a left-side portion or pump 104. The right-side portion 102 includes a right atrium 106 and a right ventricle 108. Similarly, the left-side portion 104 includes a left atrium 110 and a left ventricle 112 separated by an interventricular septum 105. Oxygen-depleted blood returning to the heart 100 from the body collects in the right atrium 106. When the right atrium 106 fills, the oxygen-depleted blood passes into the right ventricle 108 where it can be pumped to the lungs (not shown) via the pulmonary arteries 117.

Within the lungs, waste products such as carbon dioxide are removed from the blood and expelled from the body and oxygen is transferred to the blood. Oxygen-rich blood returning to the heart 100 from the lungs via the pulmonary veins (not shown) collects in the left atrium 110. The circuit between the right-side portion 102, the lungs, and the left atrium 110 is generally referred to as the pulmonary circulation. After the left atrium 110 fills, the oxygen-rich blood passes into the left ventricle 112 where it can be pumped throughout the entire body. In so doing, the heart 100 is able to supply oxygen to the body and facilitate the removal of waste products from the body.

To circulate blood throughout the body's circulatory system as described above, a beating heart performs a cardiac cycle that includes a systolic phase and a diastolic phase. During the systolic phase, or systole, the ventricular muscle cells of the right and left ventricles 108 and 112 contract to pump blood through the pulmonary circulation and throughout the body, respectively. Conversely, during the diastolic phase, or diastole, the ventricular muscle cells of the right and left ventricles 108 and 112 relax, during which the right and left atriums 106 and 110 contract to force blood into the right and left ventricles 108 and 112, respectively. Typically, the cardiac cycle occurs at a frequency between 60 and 100 cycles per minute and can vary depending on physical exertion and/or emotional stimuli, such as pain or anger.

Normally, the muscular walls of each chamber of the heart 100 contract synchronously in a precise sequence to efficiently circulate the blood as described above. In particular, both the right and left atriums 106 and 110 contract and relax synchronously. Shortly after the atrial contractions, both the right and left ventricles 108 and 112 contract and relax synchronously.

The synchronous contraction of the heart can be disrupted in an individual who suffers from congestive heart failure. For example, a patient suffering from congestive heart failure or other similar heart conditions can periodically decompensate to a point at which the individual's heart cannot pump sufficient blood to sustain even mild physical activity. In such a situation, the individual is typically hospitalized and treated with a regimen of drugs to increase hemodynamic performance and reduce cardiac demand. This drug regimen is typically applied for several days to several weeks until hemodynamic performance is improved sufficiently.

Decreased cardiac efficiency can also be treated chronically through implantation of a cardiac rhythm management system including a cardiac resynchronization therapy device. A cardiac resynchronization therapy device can apply cardiac resynchronization therapy, which is a process involving the application of an electrical stimulus to the left ventricle or both the left and right ventricles after pacing has been detected in the atria. This electrical stimulus forces septum 105 and free wall 134 of heart 100 to contract at approximately the same time, thereby resynchronizing left ventricular contraction and improving hemodynamic performance. See, for example, U.S. Pat. Nos. 6,480,742 and 6,622,040, both of which describe cardiac resynchronization devices and are hereby incorporated by reference in their entireties.

There is a need for additional systems and methods that can improve an individual's hemodynamic performance after a decompensation event.

SUMMARY

The present invention is directed to systems and methods for providing therapy for congestive heart failure. More specifically, the present invention is directed to systems and methods to provide temporary therapy for acute heart failure decompensation.

According to one aspect, the invention relates to an external device with implanted leads for providing temporary therapy to a heart of a patient. The external device includes an external module for generating electrical stimuli, a first lead coupled to the module and configured to be implanted into an atrial region of the patient's heart, and a second lead coupled to the module and configured to be implanted into a ventricular region of the patient's heart. The external module is configured to temporarily generate electrical stimuli that are delivered by at least one of the first and second leads to provide therapy to the heart.

According to another aspect, the invention relates to a system for providing temporary cardiac resynchronization therapy. The system includes a device including an external module for generating electrical stimuli, a first lead coupled to the module and configured to be implanted into an atrial region of a patient's heart, a second lead coupled to the module and configured to be implanted into a ventricular region of the patient's heart, and a storage module coupled to the external module to store data associated with physiological data measured by the device. The external module is configured to temporarily generate electrical stimuli that are delivered by at least one of the first and second leads to provide therapy cardiac resynchronization therapy to the heart. The system also includes a network coupled to the device, and a central repository coupled to the network. The data stored in the storage module of the device is uploaded through the network to the central repository.

According to yet another aspect, the invention relates to a method for providing temporary cardiac resynchronization therapy, including: providing an external module for generating electrical stimuli, a first lead coupled to the module and configured to be implanted into an atrial region of a patient's heart, and a second lead coupled to the module and configured to be implanted into a ventricular region of the patient's heart; applying temporary cardiac resynchronization therapy through application of electrical stimuli generated by the external module to the patient's heart; and discontinuing temporary cardiac resynchronization therapy after a specified period of time.

The above summary is not intended to describe each disclosed embodiment or every implementation of the present invention. The figures and detailed description that follow more particularly exemplify embodiments of the invention. While certain embodiments will be illustrated and described, the invention is not limited to use in such embodiments.

Figure 1:
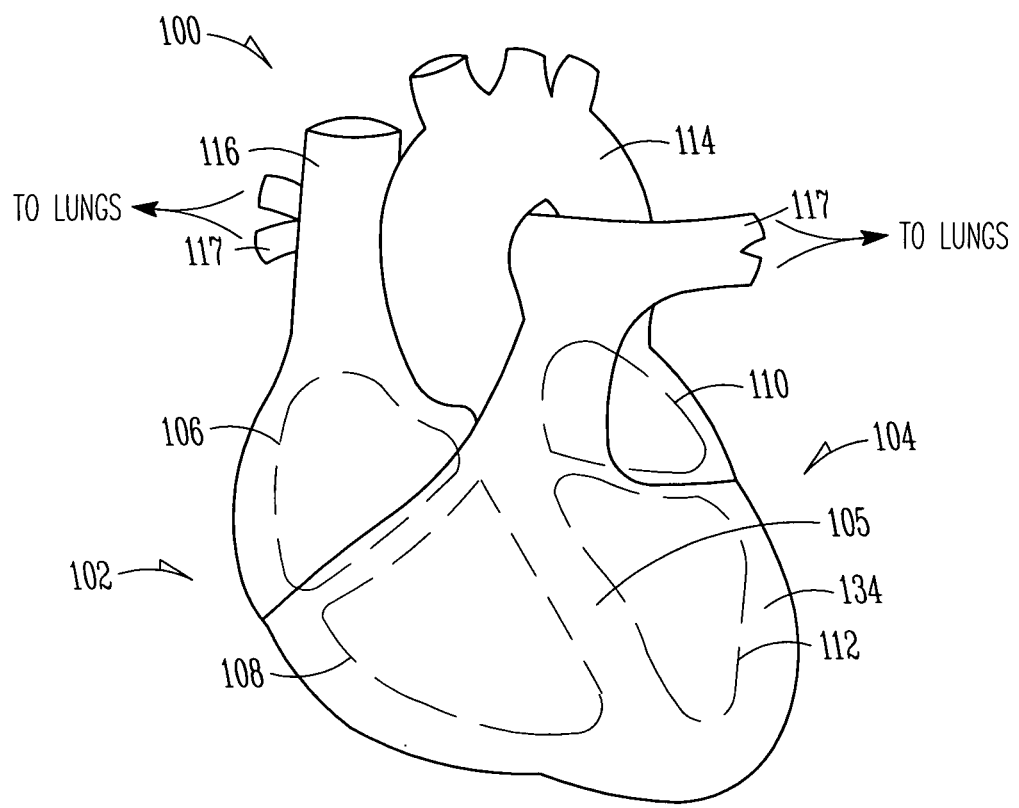
FIG. 1 is a simplified illustration depicting primary pumping components of a human heart.

While the invention is amenable to various modifications and alternative 5 forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is directed to systems and methods for providing therapy for congestive heart failure. More specifically, the present invention is directed to systems and methods to provide temporary therapy for acute heart failure decompensation.

As used herein, the term "external" is used to refer to the extracorporeal position of a component. For example, an "external device" is a device that is positioned or located outside of the body. The term "implanted" is used to refer to the intracorporeal position of a component. For example, an "implanted lead" is a lead that has been introduced into the body and associated with a heart. The term "temporary" is used to refer to a state that exists or continues for a limited time. For example, the phrase "temporary therapy" refers to a therapy that is applied for a limited period of time, in contrast to a chronic therapy that is applied indefinitely.

Example embodiments of systems and methods described herein are directed at an external device with implanted leads for providing temporary therapy to a heart of a patient. In one embodiment, the example external device includes an external module for generating electrical stimuli, a first lead coupled to the module and configured to be implanted into an atrial region of the patient's heart, and a second lead coupled to the module and configured to be implanted into a ventricular region of the patient's heart. The example external module is configured to temporarily generate electrical stimuli that are delivered by at least one of the first and second leads to provide therapy to the heart. In one embodiment, the therapy is cardiac resynchronization therapy.

In example embodiments, the external device is used to provide temporary therapy, such as cardiac resynchronization therapy, to an individual who has suffered a decompensation event. Such decompensation events include, but are not limited to, conduction abnormalities, acute myocardial infarction, or ischemic cardiomyopathy. Application of the temporary therapy can potentially improve both hemodynamic performance and reduce metabolic demand, thereby aiding in the patient's recovery.

Figure 2:
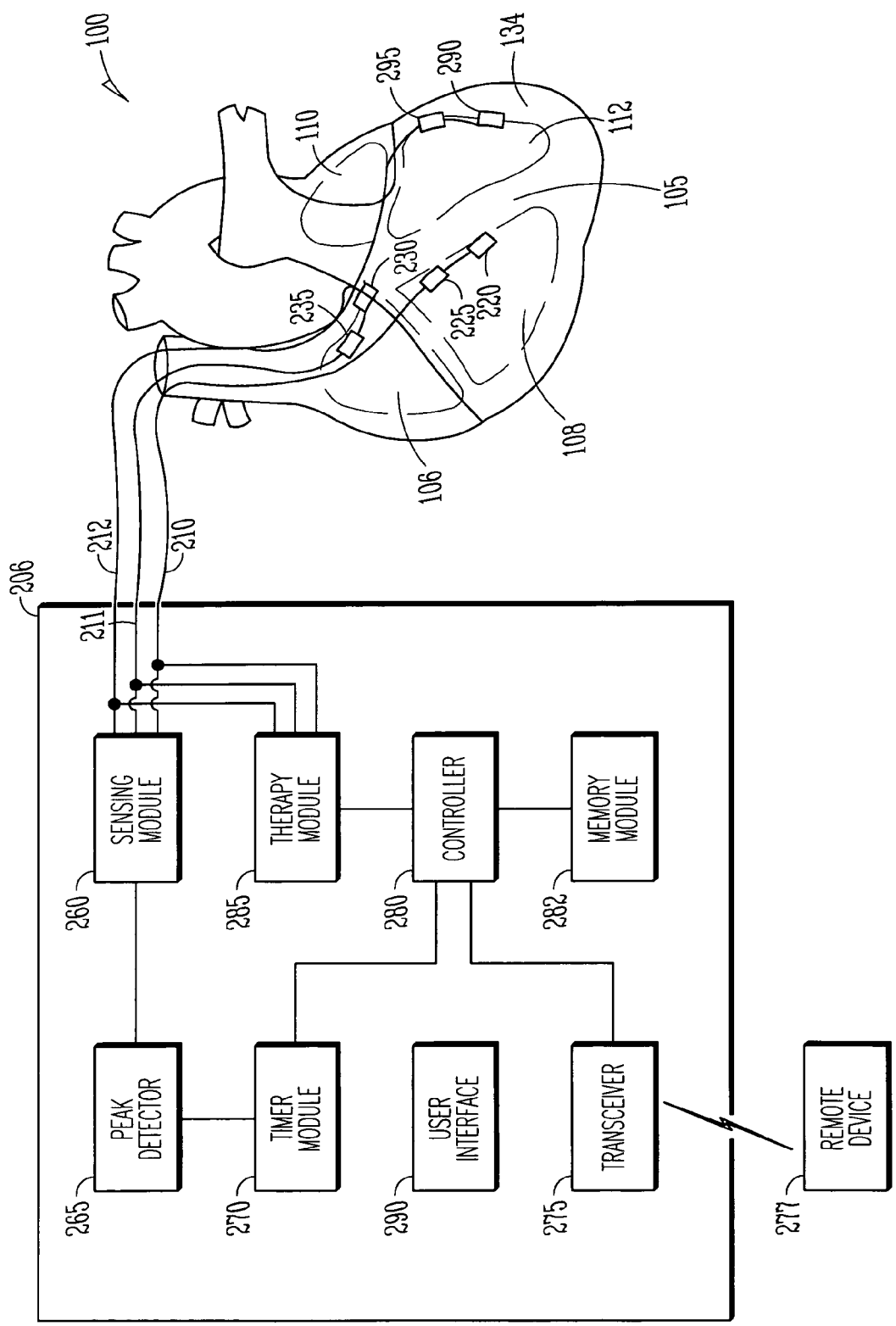
FIG. 2 is a schematic/plan drawing of an example embodiment of an external cardiac rhythm management device coupled to a human heart.

Referring now to FIG. 2, one embodiment illustrating various components of an example external device 206 is shown along with heart 100. In this embodiment, the device 206 is positioned outside of the patient's body and is coupled to leads 210, 211, and 212, which are implanted and associated with heart 100. Lead 210 is positioned in the right ventricle, lead 211 positioned in the right atrium, and lead 212 positioned in the left ventricle.

In one embodiment, leads 210, 211, and 212 include electrodes 220, 230, and 290 associated with the right ventricle, right atrium, and left ventricle, respectively. Each electrode is "associated" with the particular heart chamber by inserting it into that heart chamber, or by inserting it into a portion of the heart's vasculature that is close to that heart chamber, or by epicardially placing the electrode outside that heart chamber, or by any other technique of configuring and situating an electrode for sensing signals and/or providing therapy with respect to that heart chamber. Leads 210, 211, and 212 may alternatively also include ring electrodes 225, 235, and 295. Each electrode may be used for unipolar sensing of heart signals and/or unipolar delivery of contraction-evoking stimulations in conjunction with one or more other electrodes associated with the heart 100. Alternatively, bipolar sensing and/or therapy may be delivered, for example, between electrodes 220 and 225 of lead 210.

The device 206 includes a sensing module 260, which is coupled to one or more of the electrodes for sensing electrical depolarizations corresponding to heart chamber activity. Such electrical depolarizations of the heart tissue include atrial depolarizations, referred to as P-waves, and ventricular depolarizations, referred to as QRS complexes. The QRS complex is a rapid sequence of several signal excursions away from a baseline in sequentially switching polarity, with the largest excursion referred to as an R-wave.

A peak detector 265 is coupled to the sensing module 260 for detecting, for example, the P-wave peak from the right atrium 106, obtained by bipolar sensing between electrodes 230 and 235, or by any other sensing technique. Peak detector 165 may also sense the R-wave peak at a plurality of different sites associated with the left ventricle 112, such as at each of the electrodes 290 and 295. Sensing may be unipolar or bipolar. The peak detector 265 may detect a variety of points associated with the electrical activity of the heart 100.

A timer module 270 is coupled to the peak detector 265 for timing one or more intervals between one or more events. For example, the timer module 270 may be used to time an interval between atrial and ventricular activity.

A controller 280 is coupled to the timer module 270. The controller 280 may process the one or more intervals measured by the timer module 270. The controller 280 may store one or more calculations in a memory module 282 coupled to the controller 280.

A therapy module 285 is coupled to the controller 280. The controller 280 controls the therapy module 285, and the therapy module 285 is configured to deliver electrical impulses to the heart 100 by leads 210, 211, and/or 212. The electrical impulses may be used to stimulate activity (e.g., contraction) in one or more chambers of the heart. The therapy module 285 can be used to apply one or more therapies such as, for example, cardiac resynchronization therapy.

The device 206 also includes a transceiver 275, which is communicatively coupled to a remote device 277. The remote device 277 can communicate with the transceiver 275 to, for example, extract data from or reprogram the memory 282 of device 206, as described further below. In example embodiments, the remote device 277 can be a device on a network (see network 300 shown in FIG. 3 and described below) or a programmer.

The device 206 also includes a user interface 289. The user interface 289 allows the caregiver and/or patient to communicate with the device 206. For example, the user interface 289 can include one or more input devices, such as a mouse, keyboard, touch screen, microphone, etc., and one or more output devices, such as a liquid crystal display (LCD) or light emitting diode (LED), CRT screen, speaker, lights, vibrating motor, etc. The user interface 289 can be used, for example, to configure the therapy being applied by the device 206, or to provide information or alerts to the caregiver and/or patient.

The device 206 can generally perform one or more of the following functions: (1) therapy application; (2) data storage; (3) data analysis; (4) data forwarding; (5) patient interaction; (6) patient feedback; and (7) data communications.

For example, the device 206 is configured to operate in a variety of modes to provide one or more therapies. For example, in one mode, VVI, one or both of the ventricles 108 and 112 are sensed and paced. In another mode, VDD, one or both of the ventricles 108 and 112 are paced. In yet another mode, DDD, both the atrium 106 and one or both of the ventricles 108 and 112 are paced. Other modes can also be used.

In addition, in the example embodiment shown, the device 206 can measure and store physiological data associated with a patient. Examples of such physiological data include, without limitation, heart rate, intrinsic atrioventricular delay, heart rate variability, and the intrinsic conduction between the right ventricle 108 and the left ventricle 112.

In some embodiments, the device 206 can also analyze the physiological data. For example, the device 206 can analyze physiological data from the patient and provide an alarm if the data exceeds or drops below a given threshold. For example, device 206 can measure the patient's heart rate and alarm if the heart rate exceeds a threshold or drops below a threshold. In addition, the device 206 can present the raw data or summaries thereof to the caregiver and/or patient using the user interface 289.

Figure 3:
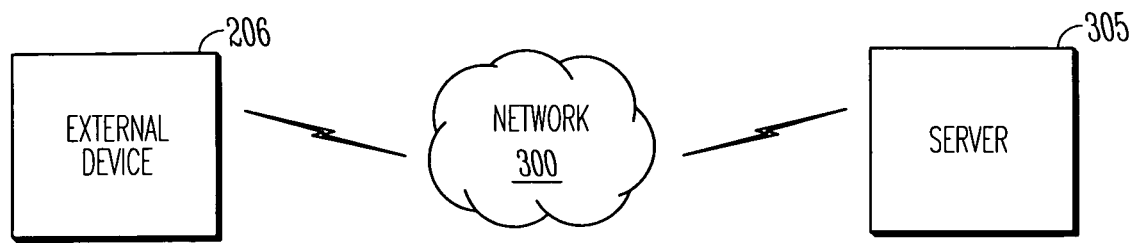
FIG. 3 is a schematic/plan drawing of an example embodiment of a cardiac rhythm management system including an external cardiac rhythm management device, a network, and a server.

As illustrated in FIG. 3, the device 206 can also forward measured data to a server 305 through a network 300. The device 206 can be coupled to the network 300 through a wired or wireless connection. The device 206 can forward collected physiological data, in raw or processed format, to the server 305 periodically or in real-time.

The server 305 can act as a central repository for the physiological data. In addition, in some embodiments, the server 305 can also perform an analysis of the data, as well as activate an alarm in the data exceeds a given threshold.

In addition, the network 300 can allow for remote access to the device 206. For example, in some embodiments, a caregiver can reconfigure device 206 remotely through the network 300.

In some embodiments, the server 305 and network 300 can be used to download one or more parameters to a chronic or permanent device implanted into a patient. In this manner, parameters calculated from data collected by the temporary device can be used to program a permanent device implanted into the patient.

Figure 4:
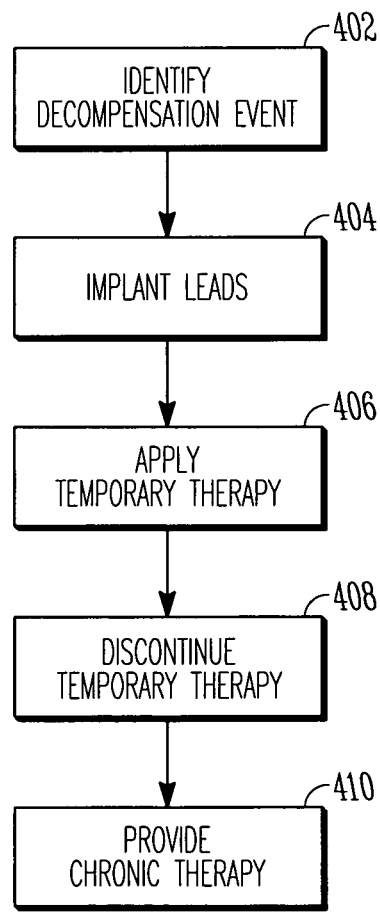
FIG. 4 is an example flow diagram illustrating a process for applying temporary cardiac resynchronization therapy to a patient.

Referring now to FIG. 4, an example method for applying therapy using device 206 is provided. At operation 402, a patient who has suffered a decompensation event is identified. Next, at operation 404, two or more leads are implanted into the patient and associated with the patient's heart. For example, in one embodiment, an atrial lead (e.g., lead 211 shown in FIG. 3) is implanted in the right atria 106 of the patient, and a ventricular lead (e.g., lead 212) is implanted into the left ventricle 112. In another embodiment, another ventricular lead (e.g., lead 210) is implanted into the right ventricle 108.

Next, control is passed to operation 406, and temporary therapy is applied using, for example, external device 206 coupled to the implanted leads. In the example embodiment, the therapy applied is cardiac resynchronization therapy, which helps to resynchronize contraction of the heart and thereby improve hemodynamic function. Other therapies can also be applied, such as, for example, bradycardia pacing, rate-responsive pacing, and anti-tachycardia pacing.

In one embodiment, therapy is applied at every heartbeat of the heart. In other embodiments, therapy is applied at periodic intervals. For example, in some embodiments, therapy is applied at every other heartbeat, or at every third heartbeat.

The therapy applied at operation 406 is temporary. In some embodiments, the therapy is applied for a relatively short period of time such as, for example, one hour, three hours, six hours, or twelve hours. In other embodiments, the temporary therapy is applied for a longer duration such as, for example, one day, three days, one week, or two weeks.

Next, in operation 408, after a given period of time, the temporary therapy applied by the device 206 is discontinued. At this point, in some situations hemodynamic performance has been improved sufficiently so that the implanted leads can be removed.

In other situations, control is passed to operation 410, wherein a chronic therapy is desirable. If chronic therapy is to be provided, an implanted cardiac rhythm management device can be used. Further, the data collected by the external device 206 during application of the temporary therapy can be analyzed and used to optimize the subsequent chronic therapy provided by an implanted device. For example, as previously noted, parameters collected by the temporary device can be downloaded to the chronic device.

Figure 5:
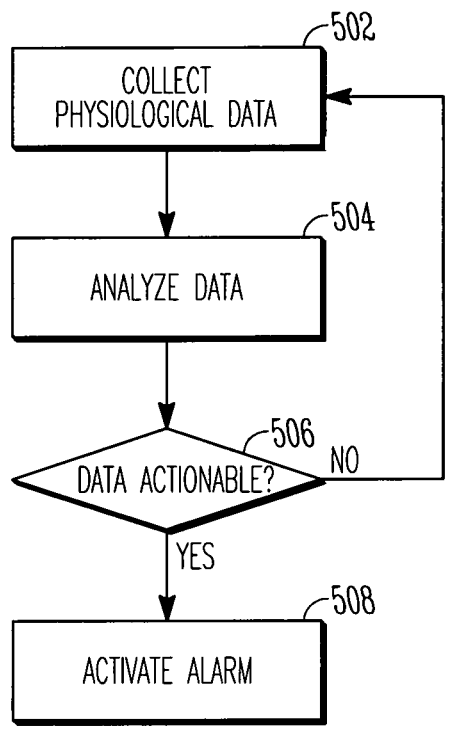
FIG. 5 is an example flow diagram illustrating a process for collection and analysis of physiological data associated with a patient by an external cardiac rhythm management device.

Referring now to FIG. 5, an example process for the analysis of physiological data collected by the external device 206 is illustrated. At operation 502, the external device 206 collects physiological data such as, for example, heart rate, intrinsic atrioventricular delay, heart rate variability, etc. At operation 504, the physiological data is analyzed. In some embodiments, this analysis can be done by device 206. In other embodiments, if the device 206 is configured to forward the data to a central repository, the analysis can be done by server 305.

Next, in operation 506, either the device 206 or sever 305 determines whether or not the data is actionable. For example, a determination can be made as to whether the data exceeds or drops below a given threshold. If the data is actionable, control is passed to operation 508, and an alarm is activated to alert the caregiver and/or patient of a specific condition. Otherwise, control is passed back to operation 502, and data collection by device 206 continues.

Although the examples described herein have been in reference to the application of cardiac resynchronization therapy, other therapies associated with the treatment of decompensation events are also applicable. For example, therapies such as bradycardia pacing, rate-responsive pacing, and anti-tachycardia pacing can also be applied.

The logical operations for device 206 can be implemented (1) as a sequence of computer implemented steps running on a computer system, and/or (2) as interconnected machine modules. This implementation is a matter of choice dependent on the performance requirements of the device 206. Accordingly, the logical operations making up the embodiments described herein are referred to as operations, steps, or modules. It will be recognized by one of ordinary skill in the art that the operations, steps, and modules may be implemented in software, in firmware, in special purpose digital logic, analog circuits, and any combination thereof without deviating from the spirit and scope of the present invention as recited within the claims attached hereto.

While the invention has been particularly shown and described with reference to preferred embodiments thereof, it will be understood by those skilled in the art that various other changes in the form and details may be made therein without departing from the spirit and scope of the invention.

What is claimed is:

1. A system comprising:
   a local external device configured to provide electrostimuli to a heart via a first lead that includes an external connection, configured to physically connect to the local external device outside of a subject's body, the first lead including an implantable electrode, configured to deliver the electrostimuli to the heart at an implanted location within the subject's body, wherein the first lead extends from the local external device outside of the subject's body and into the subject's body to the implanted location within the subject's body, wherein the local external device comprises:
      a sensing module, configured to sense an intrinsic electrical heart signal from the heart via the first lead;
      a memory module, coupled to the sensing module, the memory module configured to store physiological data about the subject obtained by sensing module using the sensed intrinsic electrical heart signal; and
      a therapy module, configured to generate energy to be provided by the electrostimuli via the first lead; and
   a transceiver, configured to send at least a portion of the physiological data over a network to a central repository that is configured to use the received portion of the physiological data to program a chronic fully implantable cardiac rhythm management device.

2. The system of claim 1, further comprising the first lead, and wherein the first lead is configured to be coupled to the local external device and is also configured to be concurrently coupled to a ventricular region of the subject's heart.

3. The system of claim 1, comprising a second lead, wherein the second lead is configured to be coupled to the local external device and is also configured to be concurrently coupled to an atrial region of the subject's heart.

4. The system of claim 1, wherein the therapy module is configured to provide cardiac resynchronization therapy to the subject.

5. The system of claim 1, wherein the therapy module is configured to deliver a specified electrostimulation therapy to the subject for less than one week.

6. The system of claim 1, wherein the therapy module is configured to deliver a specified electrostimulation therapy to the subject for less than one day.

7. The system of claim 1, wherein the therapy module is configured to deliver a specified electrostimulation therapy to the subject for less than twelve hours.

8. The system of claim 1, wherein the memory module is configured to store physiological data comprising heart rate, and wherein the transceiver is configured to send information about the heart rate over the network to the central repository for use in programming a chronic fully implantable cardiac rhythm management device.

9. The system of claim 1, wherein the memory module is configured to store physiological data comprising an intrinsic atrioventricular delay, and wherein the transceiver is configured to send information about the intrinsic atrioventricular delay over the network to the central repository for use in programming a chronic fully implantable cardiac rhythm management device.

10. The system of claim 1, wherein the memory module is configured to store physiological data comprising heart rate variability, and wherein the transceiver is configured to send information about the heart rate variability over the network to the central repository for use in programming a chronic fully implantable cardiac rhythm management device.

11. The system of claim 1, wherein the memory module is configured to store physiological data comprising an intrinsic interventricular conduction delay, and wherein the transceiver is configured to send information about the interventricular conduction delay over the network to the central repository for use in programming a chronic fully implantable cardiac rhythm management device.

12. The system of claim 1, wherein the memory module is configured to store physiological data comprising a respiration rate, and wherein the transceiver is configured to send information about the interventricular conduction delay over the network to the central repository for use in programming a chronic fully implantable cardiac rhythm management device.

13. The system of claim 1, further comprising the central repository, and wherein the central repository is configured to process the physiological data to generate an alarm if the data is actionable.

14. The system of claim 13, wherein the central repository comprises a user interface.

15. The system of claim 14, wherein the user interface is configured to enable remote programming of the local external device.

16. A method comprising:
   providing, using a local external device, electrostimuli to an implanted electrode located at an implanted location in association with a heart of a subject, the implanted electrode being electrically connected to the local external device using a lead, the lead including an external physical connection with the local external device, the local external device being disposed at a location outside of the subject's body, wherein the lead extends from the local external device outside of the subject's body and into the subject's body to the implanted location within the subject's body;
   sensing an intrinsic electrical heart signal from the heart, using the implanted electrode and the local external device;

communicating physiological data, obtained by sensing the intrinsic electrical heart signal, to a central repository; and using the physiological data to program a fully implantable cardiac rhythm management device.

17. The method of claim 16, wherein the sensing the intrinsic electrical heart signal comprises sensing atrial and ventricular intrinsic electrical heart signals.

18. The method of claim 16, wherein the providing electrostimuli comprises providing cardiac resynchronization therapy to the subject.

19. The method of claim 16, wherein providing electrostimuli comprises providing electrostimuli for a specified period that is less than one week.

20. The method of claim 16, wherein the communicating physiological data comprises communicating a heart rate, and wherein using the physiological data to program a fully implantable cardiac rhythm management device comprises using the heart rate to program the fully implantable cardiac rhythm management device.

21. The method of claim 16, wherein the communicating physiological data comprises communicating an intrinsic atrioventricular delay, and wherein using the physiological data to program a fully implantable cardiac rhythm management device comprises using the intrinsic atrioventricular delay to program the fully implantable cardiac rhythm management device.

22. The method of claim 16, wherein the communicating physiological data comprises communicating a heart rate variability, and wherein using the physiological data to program a fully implantable cardiac rhythm management device comprises using the heart rate variability to program the fully implantable cardiac rhythm management device.

23. The method of claim 16, wherein the communicating physiological data comprises communicating an intrinsic interventricular conduction delay, and wherein using the physiological data to program a fully implantable cardiac rhythm management device comprises using the intrinsic interventricular conduction delay to program the fully implantable cardiac rhythm management device.

24. The method of claim 16, wherein the communicating physiological data comprises communicating a respiration rate, and wherein using the physiological data to program a fully implantable cardiac rhythm management device comprises using the respiration rate to program the fully implantable cardiac rhythm management device.

25. A system comprising:

means for providing, using a local external device, electrostimuli to an implanted electrode located at an implanted location in association with a heart of a subject, the implanted electrode being electrically connected to the local external device using a lead, the lead including an external physical connection with the local external device, the local external device being disposed at a location outside of the subject's body, wherein the lead extends from the local external device outside of the subject's body and into the subject's body to the implanted location within the subject's body;

means for sensing an intrinsic electrical heart signal from the heart, using the implanted electrode and the local external device;

means for communicating physiological data, obtained by sensing the intrinsic electrical heart signal, to a central repository; and means for using the physiological data to program a fully implantable cardiac rhythm management device.

* * * * *